(12) United States Patent
Jenko et al.

(10) Patent No.: US 9,963,472 B2
(45) Date of Patent: May 8, 2018

(54) STABLE PANTETHEINE DERIVATIVES FOR THE TREATMENT OF PANTOTHENATE KINASE ASSOCIATED NEURODEGENERATION (PKAN) AND METHODS FOR THE SYNTHESIS OF SUCH COMPOUNDS

(71) Applicants: ACIES BIO D.O.O., Ljubljana (SI); RIJKSUNIVERSITEIT GRONINGEN, Groningen (NL); ACADEMISCH ZIEKENHUIS GRONINGEN, Groningen (DE)

(72) Inventors: Branko Jenko, Ig (SI); Gregor Kosec, Ljubljana (SI); Hrvoje Petkovic, Ljubljana (SI); Ajda Podgorsek Berke, Ljubljana (SI); Jerca Pahor, Skofja Loka (SI); Alen Cusak, Ljubljana (SI); Oda Cornelia Maria Sibon, Groningen (NL); Balaji Srinivasan, Groningen (NL)

(73) Assignees: ACIES BIO D.O.O., Ljubljana (SI); RIJKSUNIVERSITEIT GRONINGEN, Groningen (NL); ACADEMISCH ZIEKENHUIS GRONINGEN, Groningen (NL)

( * ) Notice: Subject to any disclaimer, the term of this patent is extended or adjusted under 35 U.S.C. 154(b) by 0 days. days.

(21) Appl. No.: 15/034,244

(22) PCT Filed: Oct. 29, 2014

(86) PCT No.: PCT/EP2014/073258
§ 371 (c)(1),
(2) Date: May 4, 2016

(87) PCT Pub. No.: WO2015/063177
PCT Pub. Date: May 7, 2015

(65) Prior Publication Data
US 2016/0297840 A1    Oct. 13, 2016

(30) Foreign Application Priority Data

Nov. 4, 2013   (EP) .................................... 13191457

(51) Int. Cl.
*C07F 9/09*        (2006.01)
(52) U.S. Cl.
CPC .................................. *C07F 9/091* (2013.01)
(58) Field of Classification Search
CPC ...................................................... C07F 9/091
See application file for complete search history.

(56) References Cited

FOREIGN PATENT DOCUMENTS

| GB | 749715 A | 5/1956 |
|---|---|---|
| WO | 2003/008626 A2 | 1/2003 |

(Continued)

OTHER PUBLICATIONS

Bertam et al. Pharmacological Research 50 (2004) 385-396.*

(Continued)

*Primary Examiner* — Angela C Brown-Pettigrew
(74) *Attorney, Agent, or Firm* — Cooley LLP; Heidi A. Erlacher; Xixi Sun (57) ABSTRACT

The invention relates to (S)-acyl-4'-phosphopantetheine derivatives, methods of their synthesis, and related medical uses of such compounds. Preferred medical uses relate to the treatment of neurodegenerative diseases, such as PKAN.

8 Claims, 3 Drawing Sheets

(56) References Cited

FOREIGN PATENT DOCUMENTS

| WO | 2012/017400 | A1 | 2/2012 | |
|---|---|---|---|---|
| WO | 2013/163576 | A1 | 10/2013 | |
| WO | WO 2013/163576 | * | 10/2013 | ............... C07F 9/24 |

OTHER PUBLICATIONS

Scarpini et al. Lancet Neurol 2003; 2: 539-47.*
Quinn British Medical Journal, vol. 310, No. 6979 (Mar. 4, 1995), pp. 575-579.*
Sausville et al. (Cancer Research, 2006, vol. 66, pp. 3351-3354).*
Johnson et al. (British J. of Cancer, 2001, 84(10):1424-1431).*
International Search Report and Written Opinion corresponding International Application No. PCT/EP2014/073258 dated Dec. 23, 2014.
Zhuang et al., "Divergence of Function in the Hot Dog Fold Enzyme Superfamily: The Bacterial Thioesterase YciA", Biochemistry, vol. 47, No. 9, Mar. 1, 2008, pp. 2789-2796.
Nikawa et al., Inhibitory Effects of Long-Chain Acyl Coenzyme A Analogues on Rat Liver Acetyl Coenzyme A Carboxylase, FEBS Letters, vol. 102., No. 2, Jun. 15, 1979, pp. 223-226.
Borgaro et al., "Substrate Recognition by [beta]-Ketoacyl-ACP Synthases", Biochemistry, vol. 50, No. 49, Dec. 13, 2011, pp. 10678-10686.
Bartling et al., "Steady-State Kinetics and Mechanism of LpxD, the N-Acyltransferase of Lipid A Biosynthesis", Biochemistry, vol. 47, No. 19, May 1, 2008, pp. 5290-5302.
Luo et al., "Role of Active Site Binding Interactions in 4-Chlorobenzoyl-Coenzyme A Dehalogenase Catalysis", Biochemistry, vol. 40, No. 51,Dec. 1, 2001, pp. 15684-15692.
Hoffmann et al., "Identification of the Enzymatic Active Site of Tobacco Caffeoyl-coenzyme A 0-Methyltransferase by Site-directed Mutagenesis", The Journal of Biological Chemistry, vol. 276, No. 39, Jul. 17, 2001, pp. 36831-36838.
Gerngross et al., "Enzyme-Catalyzed Synthesis of Poly[(R)-(–)-3-Hydroxybutyrate]: Formation of Macroscopic Granules In Vitro", Proceedings of the National Academy of Sciences, vol. 92, No. 14, Jul. 3, 1995, pp. 6279-6283.
Srivastava et al., ""Dehydrogenase" and "Oxidase" Reactions of Medium-Chain Fatty Acyl-CoA Dehydrogenase Utilizing Chromogenic Substrates: Role of the 3',5'-Adenosine Diphosphate Moiety of the Coenzyme A Thioester in Catalysis", Biochemistry, vol. 34, No. 14, Apr. 1, 1995, pp. 4625-4632.
Negrel et al., "The Biosynthesis of Feruloyltyramine in Nicotiana Tabacum", Phytochemistry, vol. 23, No. 12, Jan. 1, 1984, pp. 2797-2801.
Negrel et al., "The Phosphohydrolysis of Hydroxycinnamoyl-Coenzyme A Thioesters in Plant Extracts", Phytochemistry, vol. 23, No. 1, Jan. 1, 1984, pp. 31-34.
Mejean et al., "In Vitro Reconstitution of the First Steps of Anatoxin-a Biosynthesis in Oscillatoria PCC 6506: From Free L-Proline to Acyl Carrier Protein Bound Dehydroproline", Biochemistry, vol. 49, No. 1, Jan. 12, 2010, pp. 103-113.
Mandel et al., "Modular Synthesis of Pantetheine and Phosphopantetheine", Organic Letters, vol. 6, No. 26, Dec. 1, 2004, pp. 4801-4803.
Siudeja et al., "Impaired Coenzyme A metabolism affects histone and tubulin acetylation in Drosophila and human cell models of pantothenate kinase associated neurodegeneration", EMBO Molecular Medicine, vol. 3, No. 12, Oct. 14, 2011, pp. 755-766.
Rabinkov et al., "Interaction of acetyl-CoA fragments with rat liver acetyl-CoA carboxylase", European Journal of Biochemistry, vol. 193, No. 2, Oct. 1, 1990, pp. 351-353.
Hecker et al., "Prodrugs of Phosphates and Phosphonates", Journal of Medicinal Chemistry, vol. 51, No. 8, Apr. 24, 2008, pp. 2328-2345.

Hwang et al., "Enzymatic and cellular study of a serotonin N-acetyltransferase phosphopantetheine-based prodrug", Bioorganic & Medicinal Chemistry, vol. 15, No. 5, Jan. 31, 2007, pp. 2147-2155.
Baddiley et al., "Coenzyme A. Part VIII. The Synthesis of Pantetheine 4'-Phosphate (Acetobacter Stimulatory actor), a Degradation Product of the Coenzyme", The Journal of the Chemical Society, Issue 0, Jan. 1, 1953, pp. 1610-1615.
Hashimoto et al., "A Total Synthesis of Coenzyme A by Oxidation-Reduction Condensation", Chemistry Letters, 1972, pp. 595-598.
Hwang et al., "Efficient Synthesis of Phosphorylated Prodrugs with Bis(POM)-phosphoryl Chloride", Organic Letters, vol. 6, No. 10, Feb. 17, 2004, pp. 1555-1556.
Itoh et al., "Synthesis and Analysis of Substrate Analogues for UDP-Galactopyranose Mutase: Implication for an Oxocarbenium Ion Intermediate in the Catalytic Mechanism", Organic Letters, vol. 9, No. 5, 2007, pp. 879-882.
King et al., "Phosphates of Pantotenic Acid 1,2", Science, vol. 112, Nov. 10, 1950, pp. 562-565.
King et al., "Synthesis and Properties of Pantothenic Acid Monophosphates", J. Biol. Chem., vol. 191, 1951, pp. 515-521.
Kopevevich et al., "Investigations in the Field of Coenzyme A. V. Synthesis of 4'Phosphate-D-Pantetheine", UDC, 1967, pp. 629-630.
Lee et al., "Investigation of the Solution Conformation of Coenzyme A and Its Derivatives by Hodrogen-1 and Phosphorus-31 Fast Fourier Transform Nuclear Magnetic Resonance Spectroscopy", Journal of the American Chemical Society, vol. 97, No. 5, Mar. 5, 1975, pp. 1225-1236.
Mandel et al., "Modular Synthesis of Pantetheine and Phosphopantetheine", Organic Letters, vol. 6, No. 26, 2004, pp. 4801-4803.
Rana et al., "Pantethine rescues a Drosophila model for pantothenate kinase-associated neurodegeneration", PNAS, vol. 107, No. 15, Apr. 13, 2010, pp. 6988-6993.
Ruda et al., "Synthesis and Biological Evaluation of Phosphate Prodrugs of 4-Phospho-Derythronohydroxamic Acid, an Inhibitor of 6-Phosphogluconate Dehydrogenase", ChemMedChem, vol. 2, 2007, pp. 1169-1180.
Schultz, "Prodrugs of Biologically Active Phosphate Esters", Science Direct, Bioorganic & Medicinal Chemistry, vol. 11, 2003, pp. 885-898.
Siudeja et al., "Impaired Coenzyme A metabolism affects histone and tubulin acetylation in Drosophila and human cell models of pantothenate kinase associated neurodegeneration", EMBO Molecular Medicine, vol. 3, 2011, pp. 755-766.
Siudeja et al., "Cofilin/Twinstar Phosphorylation Levels Increase in Response to Impaired Coenzyme A Metabolism", PLOS One, vol. 7, Issue 8, Aug. 2012, pp. 1-9.
Strauss et al., "Mechanistic Studies on Phosphopantothenoylcysteine Decarboxylase: Trapping of an Enethiolate Intermediate with a Mechanism-Base Inactivating Agent", Biochemistry, vol. 43, 2004, pp. 15520-15531.
Wittwer et al., "Metabolism of Pantethine in Cystinosis", The Journal of Clinical Investigation, Inc., vol. 76, Oct. 1985, pp. 1665-1672.
Zhou et al., "A novel pantothenate kinase gene (PANK2) is defective in Hallervorden-Spatz syndrome", Letter, Nature Genetics, vol. 28, Aug. 2001, pp. 345-349.
Banns, H. et al. "The Synthesis of Acetylcholine from Acetyl-CoA, Acetyl-Dephospho-CoA and Acetylpantetheine Phosphate by Choline Acetyltransferase", Journal of Neurochemistry, 1977, vol. 29, p. 433-437.
Geib, N. et al. "New insights into the first oxidative phenol coupling reaction during vancomycin biosynthesis", Bioorganic Medicinal Chemistry Letters, 2008, vol. 18, p. 3081-3084.
Hartmann, D. et al. "Spatial Arrangement of Coenzyme and Substrates Bound to L-3-Hydroxyacyl-CoA Dehydrogenase As Studied by Spin-Labeled Analogues of $NAD^+$ and $CoA^+$", Biochemistry, 1991, vol. 30, p. 2782-2790.
Hu, L. et al. "Predicting Biological Functions of Compounds Based on Chemical-Chemical Interactions", PLoS One, 2011, vol. 6, Issue 12, e29491, 9 pages.

(56) References Cited

OTHER PUBLICATIONS

Kopp, F. et al. "Peptide Macrocyclization: The Reductase of the Nostocyclopeptide Synthetase Triggers the Self-Assembly of a Macrocyclic Imine", Journal of American Chemical Society, 2006, vol. 128, p. 16478-16479.

Luo, L. et al. "Role of Active Site Binding Interactions in 4 Chlorobenzoyl-Coenzyme A Dehalogenase Catalysis", Biochemistry, 2001, vol. 40, p. 15684-15692.

Nguyen, T. et al. "New Substrates and Inhibitors of 3-Hydroxy-3-methylglutaryl-CoA Reductase", Hoppe-Seyler's Z. Physiol. Chem., 1984, vol. 365, p. 1-8.

Ploskon, E. et al. "Recognition of Intermediate Functionality by Acyl Carrier Protein over a Complete Cycle of Fatty Acid Biosynthesis", Chemistry & Biology, 2010, vol. 17, p. 776-785.

Robins, L. et al. "Structural Basis for the Sugar Nucleotide and Acyl-Chain Selectivity of Leptospira interrogans LpxA", Biochemistry 2009, vol. 48, p. 6191-6201.

Singh, M. et al "S-Acetyl Phosphopantetheine: Deacetyl Citrate Lyase S-Acetyl", Biochemical and Biophysical Research Communications, 1973, vol. 53, No. 1, 9 pages.

Velikodvorskaia, V. et al. "Study of the Substrate Specificity of Acetyl-COA-Carboxyase of the Liver's Liver", Biohemia, 1990, p. 1018-1024. (Machine translation).

Tran, L. et al. "Insights into Protein-Protein and Enzyme-Substrate Interactions in Modular Polyketide Synthases", Chemistry & Biology, 2010, vol. 17, p. 705-716.

Vitali, F. et al. "Production of vancomycin aglycone conjugated to a peptide carrier domain derived from a biosynthetic non-ribosomal peptide synthetase", Chem. Communication, 2003, p. 2718-2719.

Yurgidevich, V. P. et al. "Some prerequisites for use of pantothenic acid preparations in integrated treatment of rheumatism", Chemistry, Biochemical Functions and use of Pantothenic Acid, 1977, p. 2-6.

\* cited by examiner

STABLE PANTETHEINE DERIVATIVES FOR THE TREATMENT OF PANTOTHENATE KINASE ASSOCIATED NEURODEGENERATION (PKAN) AND METHODS FOR THE SYNTHESIS OF SUCH COMPOUNDS

This application is a national phase of International Application No. PCT/EP2014/073258 filed Oct. 29, 2014 and published in the English language, which claims priority to Application No. EP 13191457.4 filed Nov. 4, 2013.

FIELD OF THE INVENTION

The present invention relates to pantetheine derivatives, their synthesis and medical uses thereof.

BACKGROUND OF THE INVENTION

Pantothenate kinase-associated neurodegeneration (PKAN) is a rare genetic neurodegenerative disease. The disease is caused by mutations in the gene coding for pantothenate kinase 2 (PANK2). Pantothenate kinase 2 phosphorylates pantothenate to 4'-phosphopantothenate in the de novo biosynthesis pathway of coenzyme A. In PKAN patients, PANK2 (one of the four PANK isoforms known in humans and localized to the mitochondria) is affected and leads to severe neurodegeneration and premature death (Zhou, B. et al. Nat. Genet., 2001, 28, 345).

Pantothenate, 4'-phosphopantothenate, pantetheine and 4'-phosphopantetheine have all been suggested as potential agents for the treatment of PKAN. For example, 4'-phosphopantothenate and 4'-phosphopantetheine, both intermediates of the CoA metabolic pathway downstream of the pantothenate kinase step, were envisioned as potential treatment options for PKAN (Zhou, B. et al. Nat. Genet., 2001, 28, 345, WO 2003/008626). Pantethine (the disulfide of pantetheine) has been shown to rescue a *Drosophila* model of PKAN (Rana, A. et al., PNAS, 2010, 107, 6988).

The use and testing of phosphorylated derivatives of pantothenate and pantetheine is hampered by a lack of suitable methods of preparation and purification procedures. Most research on the synthesis of various phosphorylated pantothenic acid derivatives has been done a long time ago, when the availability of analytical techniques was limited. Therefore, in many cases the structure and purity of products were just assumed, but not otherwise established. Moreover, in most cases the procedures are not well described and their reproducibility is questionable (King, T. E. et al. J. Biol. Chem., 1951, 191, 515; King, T. E. Science, 1950, 112, 562; J. Baddiley and E. M. Thain, J. Chem. Soc., 1953, 1610; Kopelevich, V. M., Khim. Farm. Zh., 1967, 11, 26; Hashimoto, Chem. Lett., 1972, 595).

Recently, a chemical synthesis of 4'-phosphopantothenate was described. The described synthesis method is a tedious 6-step synthesis procedure (Strauss et al., Biochemistry, 2004, 43, 15520). In the same publication an older synthesis method for 4'-phosphopantetheine and 4'-phosphopantothenoyl cysteine is disclosed.

Although pantethine is a potent compound rescuing the *Drosophila* PKAN model, in serum pantethine is rapidly converted by pantetheinases to vitamin B5 and cysteamine (Wittwer et al., J. Clin. Invest., 1985, 76, 1665) and therefore the compound pantethine is less likely to be an effective treatment for PKAN. This is confirmed by our own unpublished observations.

While a medical use of 4'-phosophopantetheine has already been speculated upon, a medical use of (S)-acyl-4'-phosphopantetheine derivatives has heretofore not been envisioned. In particular, it has not been suggested that such compounds could be useful in the treatment of neurodegenerative diseases, such as PKAN.

As a member of the group of (S)-acyl-4'-phosphopantetheine derivatives, (S)-acetyl-4'-phosphopantetheine has been structurally described (Lee, C-H. and Sarma, R. H., JACS, 1975, 97, 1225). However, an economically viable chemical synthesis method, or a possible medical use have not been reported for this compound.

(S)-benzoyl-4'-phosphopantetheine has been described as an intermediate in the synthesis of CoA derivatives (WO2012/17400). However, a pharmaceutical use of this compound was not envisaged.

Methods to increase the efficacy of compounds in medical treatment are known, in particular methods to increase the ability of pharmaceutical compounds to penetrate through membranes, or the blood-brain barrier. The medical use of phosphorylated compounds was often found to be limited by the compounds' poor ability to penetrate cell membranes. This has been attributed to the negative charge on the phosphate group which does not easily pass through cell membranes. Therefore, masking of the phosphate group, to yield a neutralized form, and to use the masked compound as a prodrug, allows the delivery of the medicament to the interior of the cells, where esterases present in the cells may subsequently cleave the protection groups from the phosphate groups, to release the active form of the drug. Thereby the bioavailability of biologically active phosphorylated compounds can be increased (Schultz, K. Bioorg. Med. Chem., 2003, 11, 885). Commonly used masking groups for this purpose are acyloxyalkyl groups, such as pivaloyloxymethyl (POM) and acetoxymethyl (AM). POM derivatives specifically have been shown to be stable in buffer and plasma.

SUMMARY OF THE INVENTION

Against this background, it is an object of the invention to provide structurally novel compounds useful for treating neurodegenerative diseases, such as PKAN. It is another object of the invention to provide novel compounds useful for treating neurodegenerative diseases, such as PKAN, which compounds are more effective in treating the disease. It is another object of the invention to provide novel compounds useful for treating neurodegenerative diseases, such as PKAN, which compounds have less side effects, e.g., show decreased toxicity, when treating the disease. It is further an object of the invention to provide novel compounds useful for treating neurodegenerative diseases, which compounds are more stable in human serum.

It is another object of the invention to provide novel medical uses of compounds derived from intermediates of the coenzyme-A biosynthetic pathway. The present invention also relates to treatment methods using compounds of the invention, and to medicaments useful in treating neurodegenerative disorders, such as PKAN. The invention also relates to effective synthesis methods for compounds of the invention and compounds useful in treatment methods of the invention.

In one embodiment, the present invention relates to thioester derivatives of 4'-phosphopantetheine, such as (S)-acyl-4'-phosphopantetheines, i.e., (S)-acyl-4'-phosphopantetheine derivatives, and their use for the treatment of neurodegenerative disorders, such as PKAN.

The present invention also relates to synthesis methods of (S)-acyl-4'-phosphopantetheines and diverse other derivatives of 4'-phosphopantetheine.

The present invention thus relates to a compound having the structural formula:

(Structure I)

wherein:

$R_1$ is —H, unsubstituted or substituted alkyl, unsubstituted or substituted alkenyl, substituted or unsubstituted cycloalkyl, substituted or unsubstituted aryl, substituted or unsubstituted arylalkyl, substituted or unsubstituted non-aromatic heterocyclyl, substituted or unsubstituted aromatic heterocyclyl, substituted or unsubstituted heterocyclylalkyl, —$COR_{11}$, —$C(O)OR_{11}$, —$C(O)NR_{11}R_{12}$, —$C=NR_{11}$, —CN, —$OR_{11}$, —$OC(O)R_{11}$, —$NR_{11}R_{12}$, —$NR_{11}C(O)R_{12}$, —$NO_2$, —$N=CR_{11}R_{12}$ or -halogen; preferably $C_1$-$C_{10}$ alkyl, more preferably -methyl, -ethyl, -propyl or -butyl, such as t-butyl, most preferred -methyl;

$R_2$ and $R_3$ are independently selected from the group consisting of: -methyl, -ethyl, -phenyl, acetoxymethyl (AM), pivaloyloxymethyl (POM), $R_2$ and $R_3$ jointly form a structure selected from the group consisting of:

wherein $R_4$ is —H or -alkyl, preferably -methyl;
$R_5$ is —H or -alkyl, preferably $C_1$-$C_4$ alkyl, most preferably -methyl or t-butyl;
$R_6$ is —H, -alkyl or —$CH_2(CO)OCH_3$;
$R_7$ is —H, -alkyl or -halogen;
$R_8$ is —H, -alkyl, preferably t-butyl;
$R_9$ is —H, -alkyl, preferably $C_1$-$C_4$ alkyl;
$R_{10}$ is —H, -alkyl, preferably $C_1$-$C_4$ alkyl;
$R_{11}$ and $R_{12}$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen;

with the proviso that the compound is not (S)-acetyl-4'-phosphopantetheine or (S)-benzoyl-4'-phosphopantetheine; or a pharmaceutically acceptable salt or solvate thereof.

Preferred alkyl groups in the above definitions are -methyl, -ethyl, -propyl, -butyl, preferably t-butyl.

The D stereoisomer of Structure I is generally preferred.

In structures of the invention, a straight line overlayed by a wavy line denotes the covalent bond of the respective residue to the Structure I.

In preferred embodiments, $R_2$ and $R_3$ are identical residues. Bis-POM and bis-AM structures are particularly preferred.

Another aspect of the invention relates to a compound having the structural formula:

(Structure I)

wherein:

$R_1$ is —H, unsubstituted or substituted alkyl, unsubstituted or substituted alkenyl, substituted or unsubstituted cycloalkyl, substituted or unsubstituted aryl, substituted or unsubstituted arylalkyl, substituted or unsubstituted non-aromatic heterocyclyl, substituted or unsubstituted aromatic heterocyclyl, substituted or unsubstituted heterocyclylalkyl, —$COR_{11}$, —$C(O)OR_{11}$, —$C(O)NR_{11}R_{12}$, —$C=NR_{11}$, —CN, —$OR_{11}$, —$OC(O)R_{11}$, —$NR_{11}R_{12}$, —$NR_{11}C(O)R_{12}$, —$NO_2$, —$N=CR_{11}R_{12}$ or -halogen; preferably $C_1$-$C_{10}$ alkyl, more preferably -methyl, -ethyl, -propyl or -butyl, such as t-butyl, most preferred is -methyl, most preferred -methyl;

$R_2$ and $R_3$ are independently selected from the group consisting of: —H, -methyl, -ethyl, -phenyl, acetoxymethyl (AM), pivaloyloxymethyl (POM), $R_2$ and $R_3$ jointly form a structure selected from the group consisting of:

wherein $R_4$ is —H or -alkyl, preferably -methyl;

$R_5$ is —H or -alkyl, preferably $C_1$-$C_4$ alkyl, most preferably -methyl or t-butyl;

$R_6$ is —H, -alkyl or —$CH_2(CO)OCH_3$;

$R_7$ is —H or -alkyl or -halogen;

$R_8$ is —H or -alkyl, preferably t-butyl;

$R_9$ is —H, -alkyl, preferably $C_1$-$C_4$ alkyl;

$R_{10}$ is —H, -alkyl, preferably $C_1$-$C_4$ alkyl;

$R_{11}$ and $R_{12}$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen;

or a pharmaceutically acceptable salt or solvate thereof;

for use as a medicament.

In particularly preferred embodiments of any aspect of the invention, $R_2$ and $R_3$ are both -ethyl or both -phenyl. In other preferred embodiments, $R_2$ is -ethyl and $R_3$ is -phenyl, or $R_3$ is -ethyl and $R_2$ is -phenyl.

In a second preferred embodiment, $R_2$ and $R_3$ are both where $R_4$ is —H, methyl; $R_5$ is alkyl, such as methyl or t-butyl. Preferably $R_4$ is —H and $R_5$ is -methyl. Hence, $R_2$ and $R_3$ may both be acetoxymethyl (AM). In another embodiment $R_4$ is —H and $R_5$ is t-butyl. Hence, $R_2$ and $R_3$ may both be pivaloyloxymethyl (POM).

In a third preferred embodiment, $R_2$ and $R_3$ are both

(acetooxybenzyl)

In a fourth preferred embodiment, $R_2$ and $R_3$ are both wherein $R_6$ is —H, -alkyl or —$CH_2(CO)OCH_3$.

In a fifth preferred embodiment, the phosphate group forms a cyclic phosphate according to the following structure:

wherein $R_7$ is alkyl or halogen or the cyclic phosphate includes:

wherein $R_8$ is t-butyl.

In a sixth embodiment, $R_2$ and $R_3$ are both S-[(2-hydroxyethyl)sulfidyl]-2-thioethyl (DTE), or wherein $R_9$ is alkyl, preferably -methyl, -ethyl, -propyl or -butyl, such as t-butyl.

In a seventh preferred embodiment, $R_2$ and $R_3$ are both S-acyl-2-thioethyl (SATE), or wherein $R_{10}$ is alkyl, preferably -methyl, -ethyl, -propyl or -butyl, such as t-butyl Preferred alkyl groups are -methyl, -ethyl, -propyl, -butyl, preferably t-butyl.

The D stereoisomer of Structure I is generally preferred.

In preferred embodiments, said medicament is useful in the treatment of a neurodegenerative disease, epilepsy or cancer; preferably a neurodegenerative disease or epilepsy; even more preferred a neurodegenerative disease. In particularly preferred embodiments, the neurodegenerative disease is pantothenate kinase-associated neurodegeneration (PKAN).

Hence, an aspect of the invention relates to a method of treating a neurodegenerative disease, epilepsy or cancer (preferably a neurodegenerative disease or epilepsy; even more preferred a neurodegenerative disease) by administering to a subject in need a therapeutically effective amount of a compound according to the invention as described hereinabove. In particularly preferred embodiments, the neurodegenerative disease is pantothenate kinase-associated neurodegeneration (PKAN).

The present invention also relates to a method of producing a compound of the invention as described hereinabove, said method comprising the step of reacting 4'phosphopantothenate with an (S)-substituted mercaptoethylamine to yield (S)-substituted-4'-phosphopantetheine.

In preferred embodiments the method includes enzymatic conversion of pantothenate to 4'-phosphopantothenate prior to the step of reacting 4'phosphopantothenate with an (S)-substituted mercaptoethylamine (e.g., (S)-trityl-mercaptoethylamine) to yield (S)-substituted-4'-phosphopantetheine (e.g., (S)-trityl-4'-phosphopantetheine).

In preferred embodiments the method further comprises converting (S)-substituted-4'-phosphopantetheine (e.g., (S)-trityl-4'-phosphopantetheine) to 4'-phosphopantetheine.

In preferred embodiments the method further comprises converting 4'-phosphopantetheine by thioesterification to (S)-acyl-4'-phosphopantetheine (e.g., to (S)-acetyl-4'-phosphopantetheine).

In preferred embodiments the method further comprises formation of a phosphate ester of said (S)-acyl-4'-phosphopantetheine with a chloromethyl ester or a iodomethyl ester of a carboxylic acid.

The present invention also relates to a method of producing a compound of the invention as described hereinabove, said method comprising the steps of a) reacting pantothenate with an (S)-substituted mercaptoethylamine to yield (S)-substituted pantetheine, b) reacting the S-substituted pantetheine with a phosphorylating agent such as dibenzylchlorophosphate to obtain a phosphate ester of S-substituted 4'-phosphopantetheine such as S-trityl-4'-dibenzylphosphopantetheine and c) converting said phosphate ester of (S)-substituted-4'-phosphopantetheine (e.g., (S)-trityl-4'-dibenzylphosphopantetheine) to 4'-phosphopantetheine.

The (S)-substituent can be any of the thiol protecting groups, known in the literature, usually resulting in thioeter or thioester bond, e.g. trityl benzyl, benzoyl, stearoyl or palmitoyl group.

In preferred embodiments the method further comprises converting 4'-phosphopantetheine by thioesterification to (S)-acyl-4'-phosphopantetheine (e.g., to (S)-acetyl-4'-phosphopantetheine).

In preferred embodiments the method further comprises formation of a phosphate ester of said (S)-acyl-4'-phosphopantetheine with a chloromethyl ester or a iodomethyl ester of a carboxylic acid.

In addition, the present invention relates to a method of producing a compound of the invention as described hereinabove, said method comprising the steps of reacting the (S)-substituted pantetheine such as (S)-acylpantetheine with a phosphorylating agent such as bis[(pivaloyloxy)methyl chlorophosphate to obtain a phosphate ester of S-substituted 4'-phosphopantetheine such as bis(pivaloyloxymethyl) ester of S-acyl-4'-phosphopantetheine.

The (S)-substituent has a general formula $R_1(C=O)$— wherein $R_1$ is —H, unsubstituted or substituted alkyl, unsubstituted or substituted alkenyl, substituted or unsubstituted cycloalkyl, substituted or unsubstituted aryl, substituted or unsubstituted arylalkyl, substituted or unsubstituted non-aromatic heterocyclyl, substituted or unsubstituted aromatic heterocyclyl, substituted or unsubstituted heterocyclylalkyl, —$COR_{11}$, —$C(O)OR_{11}$, —$C(O)NR_{11}R_{12}$, —$C=NR_{11}$, —CN, —$OR_{11}$, —$OC(O)R_{11}$, —$NR_{11}R_{12}$, —$NR_{11}C(O)R_{12}$, —$NO_2$, —$N=CR_{11}R_{12}$ or -halogen; preferably $C_1$-$C_{10}$ alkyl, more preferably -methyl, -ethyl, -propyl or -butyl, such as t-butyl, most preferred is -methyl, most preferred -methyl.

DETAILED DESCRIPTION OF THE INVENTION

The term "neurodegenerative disease", in accordance with the present invention, shall be interpreted as having the meaning commonly understood in the art. In preferred embodiments, the "neurodegenerative disease" is selected from the group consisting of: Pantothenate kinase-associated neurodegeneration (PKAN), Alzheimer's disease, Parkinson's disease, Huntington's disease, Amyotrophic lateral sclerosis (ALS), Dementia Ataxia telangiectasia, Autosomal dominant cerebellar ataxia, Batten disease, Corticobasal degeneration, Creutzfeldt-Jakob disease, Fatal familial insomnia, Hereditary motor and sensory neuropathy with proximal dominance, Infantile Refsum disease, JUNQ and IPOD, Locomotor ataxia, Lyme disease, Machado-Joseph disease, Mental retardation and microcephaly with pontine and cerebellar hypoplasia, Multiple system atrophy, Neuroacanthocytosis, Niemann-Pick disease, Pontocerebellar hypoplasia, Refsum disease, Sandhoff disease, Shy-Drager syndrome, Spinocerebellar ataxia, Subacute combined degeneration of spinal cord, Subacute sclerosing panencephalitis, Tabes dorsalis, Tay-Sachs disease, Toxic encephalopathy, and Wobbly hedgehog syndrome. Preferred neurodegenerative disorders, in the context of the present invention are Pantothenate kinase-associated neurodegeneration (PKAN), Alzheimer's disease, Parkinson's disease, Huntington's disease, Amyotrophic lateral sclerosis (ALS), Dementia; most preferably Pantothenate kinase-associated neurodegeneration (PKAN).

Within the context of the present invention, "alkyl" refers to a straight or branched hydrocarbon chain radical consisting of carbon and hydrogen atoms, containing no saturation, having one to eight carbon atoms, and which is attached to the rest of the molecule by a single bond, e.g., methyl, ethyl, n-propyl, i-propyl, n-butyl, t-butyl, n-pentyl, etc. Alkyl radicals may be optionally substituted by one or more substituents such as a aryl, halo, hydroxy, alkoxy, carboxy, cyano, carbonyl, acyl, alkoxycarbonyl, amino, nitro, mercapto, alkylthio, etc. If substituted by aryl we have an "Aralkyl" radical, such as benzyl and phenethyl.

"Alkenyl" refers to an alkyl radical having at least two carbon atoms covalently connected by a double bond.

"Cycloalkyl" refers to a stable 3- to 10-membered monocyclic or bicyclic radical which is saturated or partially saturated, and which consist solely of carbon and hydrogen atoms, such as cyclohexyl or adamantyl. Unless otherwise defined, the term"cycloalkyl" is meant to include cycloalkyl radicals which are optionally substituted by one or more substituents such as alkyl, halo, hydroxy, amino, cyano, nitro, alkoxy, carboxy, alkoxycarbonyl.

"Aryl" refers to single and multiple ring radicals, including multiple ring radicals that contain separate and/or fused aryl groups. Typical aryl groups contain from 1 to 3 separated or fused rings and from 6 to about 18 carbon ring atoms, such as phenyl, naphthyl, indenyl, fenanthryl or anthracyl radical. The aryl radical may be optionally substituted by one or more substituents such as hydroxy, mercapto, halo, alkyl, phenyl, alkoxy, haloalkyl, nitro, cyano, dialkylamino, aminoalkyl, acyl, alkoxycarbonyl, etc.

"Heterocyclyl" refers to a stable 3- to 15 membered ring radical which consists of carbon atoms and from one to five heteroatoms selected from the group consisting of nitrogen, oxygen, and sulfur, preferably a 4- to 8-membered ring with one or more heteroatoms, more preferably a 5- or 6-membered ring with one or more heteroatoms. It may be aromatic or not. For the purposes of this invention, the heterocycle may be a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran, coumarine, morpholine; pyrrole, pyrazole, oxazole, isoxazole, triazole, imidazole, etc.

"Alkoxy" refers to a radical of the formula —ORa where Ra is an alkyl radical as defined above, e. g., methoxy, ethoxy, propoxy, etc.

References herein to "substituted" groups in the compounds of the present invention refer to the specified moiety that is substituted at one or more available positions by one or more suitable groups, e. g., halogen such as fluoro, chloro, bromo and iodo, cyano, hydroxyl, nitro, azido, alkanoyl such as a C1-6 alkanoyl group such as acyl and the like, carboxamido, alkyl groups including those groups having 1 to about 12 carbon atoms or from 1 to about 6 carbon atoms and more preferably 1-3 carbon atoms, alkenyl and alkynyl groups including groups having one or more unsaturated linkages and from 2 to about 12 carbon or from 2 to about 6 carbon atoms, alkoxy groups having one or more oxygen linkages and from 1 to about 12 carbon atoms or 1 to about 6 carbon atoms, aryloxy such as phenoxy, alkylthio groups including those moieties having one or more thioether linkages and from 1 to about 12 carbon atoms or from 1 to about 6 carbon atoms, alkylsulfinyl groups including those moieties having one or more sulfinyl linkages and from 1 to about 12 carbon atoms or from 1 to about 6 carbon atoms, alkylsulfonyl groups including those moieties having one or more sulfonyl linkages and from 1 to about 12 carbon atoms or from 1 to about 6 carbon atoms, aminoalkyl groups such as groups having one or more N atoms and from 1 to about 12 carbon atoms or from 1 to about 6 carbon atoms; carbocylic aryl having 6 or more carbons, particularly phenyl or naphthyl and aralkyl such as benzyl. Unless otherwise indicated, an optionally substituted group may have a substituent at each substitutable position of the group, and each substitution is independent of the other.

The term "pharmaceutically acceptable salts or solvates" refers to any pharmaceutically acceptable salt, solvate, or any other compound which, upon administration to the recipient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, prodrugs and derivatives can be carried out by methods known in the art. For instance, pharmaceutically acceptable salts of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium, ammonium, magnesium, aluminium and lithium salts, and organic alkali salts such as, for example, ethylenediamine, ethanolamine, N,N-dialkylenethanolamine, triethanolamine, glucamine and basic aminoacids salts.

The present invention generally relates to the treatment of neurodegenerative diseases and compounds useful in such treatment. In a preferred embodiment, the neurodegenerative disease is pantothenate kinase-associated neurodegeneration (PKAN).

PKAN is believed to be caused by impaired function of the enzyme pantothenate kinase 2. Pantothenate kinase is required for the synthesis of Coenzyme A (Rana, A. et al., PNAS, 2010, 107, 6988). It has been demonstrated in a fly model for PKAN, that the compound pantethine restores levels of Coenzyme A and thereby rescues all disease characteristics of PKAN (Rana, A. et al., PNAS, 2010, 107, 6988). However, the use of pantethine to treat human subjects with pantethine is limited by the fact that pantethine is not stable in human serum and in human intestines and is rapidly converted into vitamin B5 and cysteamine (Wittwer et al., J Clin Invest, 1985, 76, 1665) and pantethine is toxic to wild type flies (Rana, A. et al., PNAS, 2010, 107, 6988). The present invention overcomes this deficiency by providing treatment methods based on compounds which have improved stability in serum and which compounds are less toxic than pantethine.

In a first aspect, the present invention relates to a novel class of pharmaceuticals, for use in the treatment of neurodegenerative diseases (preferably PKAN), herein denoted as (S)-acyl-4'-phosphopantetheines. From this group of compounds only (S)-acetyl-4'-phosphopantetheine (Lee, C-H. and Sarma, R. H., JACS, 1975, 97, 1225) and (S)-benzoyl-4'-phosphopantetheine (WO 2012/017400) were structurally known. The pharmaceutical potential of this group of compounds (in particular of the known substances (S)-acetyl-4'-phosphopantetheine and (S)-benzoyl-4'-phosphopantetheine) has not been realized before the present invention.

In a second aspect, the invention relates to prodrugs that liberate biologically active (S)-acyl-4'-phosphopantetheines in mammalian cells. In these prodrugs the phosphate group is masked by moieties that facilitate the transfer of these compounds through cell membranes as well as the blood-brain-barrier. Such prodrugs have the following chemical structure:

(Structure I)

in which $R_1$ is as defined in the appended claims, or $R_1$ may be —$CH_3$, —$C_2H_5$, —$C_3H_7$, —$C_4H_9$; and $R_2$ and $R_3$ are as defined in the appended claims, or $R_2$ and $R_3$ may be —$CH_2O(CO)tBu$, —$CH_2O(CO)Me$. The D-isomer is preferred.

Phosphate ester compounds are preferred due to their increased potential to penetrate membranes or, e.g., the blood-brain barrier. Suitable methods of producing such phosphate esters of S-acyl-phosphopantetheine are well known in the art. An exemplary synthetic method is provided in Example 7. A review of other suitable methods for forming prodrugs by esterification of phosphate groups of pharmaceutically active ingredients is provided by Schultz (2003, "Prodrugs of biologically active phosphate esters", Bioorg Med Chem 11: 885), specific reference to which is hereby made, and the contents of which is incorporated herein by reference to the extent permitted.

A third aspect of the invention relates to a novel and economically viable methods for the production of (S)-acyl-4'-phosphopantetheine derivatives, as defined in the claims, including their prodrugs having a masked phosphate group. Masking of a phosphate group is preferably esterification of the phosphate group.

The present invention is based on the observation that two novel pantethine-derivatives, namely 4'-phosphopantetheine and (S)-acetyl-4'-phosphopantetheine exhibit increased stability in human serum and are less toxic when compared to pantethine. In addition, it was surprisingly found that (S)-acetyl-4'-phosphopantetheine is more effective than pantethine (and 4'-phosphopantetheine) in a drosophila disease model for PKAN.

Based on the efficient rescue of cells in neural disease models by 4'-phosphopantetheine and (S)-acetyl-4'-phosphopantetheine, the increased stability of the two compounds in serum and on the reduced toxicity of the compounds, we conclude that the group of compounds falling under the generic Structure I, as defined in the claims, is superior to all presently known PKAN therapeutics, proposed PKAN therapeutics, and/or PKAN therapeutics in development. N.b., currently there are no approved therapeutics available to halt or reverse the symptoms of PKAN. Compounds of the generic Structure I are useful therapeutics for neurodegenerative disorders of the invention, in particular for PKAN.

It is known that in fly and cell models of PKAN, the levels of protein acetylation are decreased (Siudeja et al., EMBO Mol Med 2011, 3, 755). We have shown that histone deacetylase (HDAC) inhibitors, such as Trichostatin A (TSA) and valproic acid rescue the protein acetylation defect in PKAN models. Pantethine also rescues the acetylation defects in PKAN models. The source for the acetyl group required for protein acetylation is acetyl-coenzyme A. The inventors believe that (S)-acetyl-4'-phosphopantetheine is a compound that is rapidly converted into acetyl-CoA, thereby increasing protein acetylation. For a variety of diseases HDAC inhibitors are being used and specifically the valproic acid is currently used in diseases ranging from cancer, to epilepsy, to neurodegeneration. The disadvantage is that valproic acid has severe side effects. We believe that (S)-acetyl-4'-phosphopantetheine and its derivatives according to the invention can serve as an alternative for valproic acid in restoring or increasing protein acetylation without causing severe side effects. Compounds of Structure I, such as (S)-acetyl-4'-phosphopantetheine can serve as an alternative to valproic acid in various therapies. Therefore, (S)-acyl-4'-phosphopantetheine derivatives, such as (S)-acetyl-4'-phosphopantetheine derivatives, can be used in therapy for diseases in which valproic acid is currently used. Specific examples are: cancer, epilepsy, Alzheimer's disease.

Hence, particularly preferred medical indications, in the context of the invention, are neurodegenerative diseases as defined above, in particular PKAN, but also epilepsy, and cancer.

The surprising finding that compounds of the invention show superior stability over, e.g., pantethine in serum may be explained ex post by their lower sensitivity to pantetheinases. The increased rescue potential of (S)-acylated compounds of the invention, such as (S)-acetyl-4'-phosphopantetheine over 4'-phosphopantetheine is currently not well understood, because one would expect that both molecules could equally well be converted into Coenzyme A, which is the molecule which is lacking in PKAN and most likely causing the disease. Our results show that the compounds of the invention, such as (S)-acetyl-4'-phosphopantetheine and its derivatives, have a higher rescue potential, suggesting that it is more efficiently converted into Coenzyme A, or converted directly into acetyl-CoA and this maybe beneficial. This, however, is merely speculation. The reason for the observed superior potency of the compounds of the invention in the treatment of the above mentioned diseases is really not well understood.

In the scope of this invention, we have synthesized 4'-phosphopantothenate, 4'-phosphopantetheine and (S)-acetyl-4'-phosphopantetheine and tested its ability to rescue cells in cell line models of PKAN. We demonstrated that (S)-acetyl-4'-phosphopantetheine is superior to the previously proposed 4'-phosphopantetheine (having a free sulfhydryl group), phosphopantothenate and pantethine in restoring normal growth of a PKAN cell model with impaired pantothenate kinase activity.

We have also determined that (S)-acyl-4'-phosphopantetheine and its derivatives, such as (S)-acetyl-4'-phosphopantetheine, are more stable in serum than pantethine with free sulfhydryl group.

In preferred embodiments, derivatization of the phosphate group of (S)-acyl-4'-phosphopantetheines with acyloxyalkyl groups, such as pivaloyloxymethyl (POM) and acetoxymethyl (AM) provides further advantageous properties, because such prodrug derivatives penetrate the blood-brain-barrier of mammals more easily. This is specifically important for the effective treatment of neurodegenerative diseases.

The derivatization of the phosphate group is chemically easily achieved when using (S)-acyl-4'-phosphopantetheines while, in contrast, such derivatization is much more difficult, if not impossible, to achieve in the case of 4'-phosphopantetheine. This is due to the interference of the free sulfhydryl group in the required chemical reactions.

The design a viable synthetic route from the commercially available pantothenate (vitamin B5) to (S)-acyl-4'-phosphopantetheines forms an important aspect of the present invention. Only through the availability of this synthesis route it became possible to determine the improved biological activity of the latter compounds.

Briefly, pantothenic acid is enzymatically converted to 4'-phosphopantothenate. Isolated 4'-phosphopantothenic acid is then reacted with (S)-substituted mercaptoethylamines in the presence of a coupling reagent and an activator in a solvent. (S)-trityl-4'-phosphopantetheine obtained this way is isolated from the reaction mixture followed by its conversion to 4'-phosphopantetheine. Finally, 4'-phosphopantetheine is converted to (S)-acyl-4'-phosphopantetheine by thioesterification with the corresponding thioacid, such as thioacetic acid.

Alternatively, pantothenic acid is reacted with previously prepared (S)-substituted mercaptoethylamines in the presence of a coupling reagent and an activator in a solvent. (S)-trityl-4'-pantetheine obtained this way is isolated from the reaction mixture, followed by its phosphorylation with dibenzylchlorophosphate in the presence of a base in a solvent. Removing of benzyl and trityl protecting group gives 4'-phosphopantetheine. Finally, 4'-phosphopantetheine is converted to (S)-acyl-4'-phosphopantetheine by thioesterification with the corresponding thioacid, such as thioacetic acid.

Masking the phosphate group includes the formation of phosphate esters from (S)-acyl-4'-phosphopantetheine with the corresponding chloro-methylester of the carboxylic acid, such as chloromethyl pivalate and chloromethyl acetate.

Alternatively, masking of the phosphate group can be done by phosphorylating S-substituted pantetheine such as (S)-acetyl-4'-pantetheine with a suitable phosphorylating agent such as bis[(pivaloyloxy)methyl chlorophosphate in the presence of a base in a solvent to obtain bis(pivaloyloxymethyl) ester of S-acyl-4'-phosphopantetheine The present invention further provides pharmaceutical compositions comprising a compound of invention, or a pharmaceutically acceptable salt thereof, preferably together with a pharmaceutically acceptable carrier, adjuvant, or vehicle, for administration to a patient.

Examples of pharmaceutical compositions of the invention include any solid (tablets, pills, capsules, granules etc.) or liquid (solutions, suspensions or emulsions) composition for oral, topical, parenteral or sublingual administration.

In a preferred embodiment the pharmaceutical compositions are in oral form, either solid or liquid. Suitable dose forms for oral administration (including sublingual administration) may be tablets, capsules, syrups or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

Administration of the compounds or compositions of the present invention may be by any suitable method, such as intravenous infusion, oral preparations, and intraperitoneal, intramuscular, sub-cutaneous, sublingual, topical and intravenous administration. Oral administration (in particular sublingual administration) is preferred because of the convenience for the patient and the chronic character of the diseases to be treated.

The compounds and compositions of this invention may be used with other drugs to provide a combination therapy. The other drugs may form part of the same composition, or be provided as a separate composition for administration at the same time or at different time.

A suitable dose for compounds of the invention is from 0.1 to 1000 mg/kg body weight/day, preferably 0.1 to 100 mg/kg body weight/day, more preferably 1 to 50 mg/kg body weight/day. Administration is preferably 1×, 2×, 3×, or 4× per day, preferably 1× or 2× per day.

The following structural formulae are relevant in the context of the present invention:

(pantethine)

(4'-phosphopantetheine)

(4'-phosphopantothenate)

((S)-acetyl-4'-phosphopantetheine)

((S)-acyl-4'-phosphopantetheines)

EXAMPLES

Example 1: Synthesis of (S)-acyl-4'-phosphopantetheines

Pantothenic acid was enzymatically converted to 4'-phosphopantothenate. Isolated 4'-phosphopantothenic acid was then reacted with (S)-substituted mercaptoethylamines in the presence of a coupling reagent and an activator in a solvent. (S)-trityl-4'-phosphopantetheine obtained this way was isolated from the reaction mixture, followed by its conversion to 4'-phosphopantetheine. Finally, 4'-phosphopantetheine was converted to (S)-acyl-4'-phosphopantetheine by thioesterification with the corresponding thioacid, such as thioacetic acid. In one example, the phosphate group was masked by esterification, to improve the membrane penetration potential of the compound. Masking the phosphate group was effected by the formation of phosphate esters from (S)-acyl-4'-phosphopantetheine with the corresponding halomethyl ester of the carboxylic acid, such as chloromethyl pivalate, iodomethyl pivalate, chloromethyl acetate and iodomethyl acetate.

Example 2: Increased Stability of 4'-phosphopantetheine and (S)-acetyl-4'-phosphopantetheine in Serum as Compared to Pantethine This example shows the superior stability of (S)-acetyl-4'-phosphopantetheine and 4'-phosphopantetheine in fetal calf serum (FCS) in comparison to pantethine.

Pantethine has been shown to be rapidly converted in serum by pantetheinases to vitamin B5 and cysteamine (Wittwer et al., 1985, 76, 1665). We synthesized (S)-acetyl-4'-phosphopantetheine and 4'-phosphopantetheine as described in Example 1 and subsequently evaluated the stability of these compounds in FCS.

Materials and Methods: Pantethine (purchased from Sigma), (S)-acetyl-4'-phosphopantetheine and 4'-phosphopantetheine were incubated at a final concentration of 1 mM in FCS and in PBS for 30 minutes at 37° C. After incubation, the samples were processed to remove proteins and HPLC analysis was used to assess the amount of remaining compound indicating the stability of the respective compounds.

Figure 1:
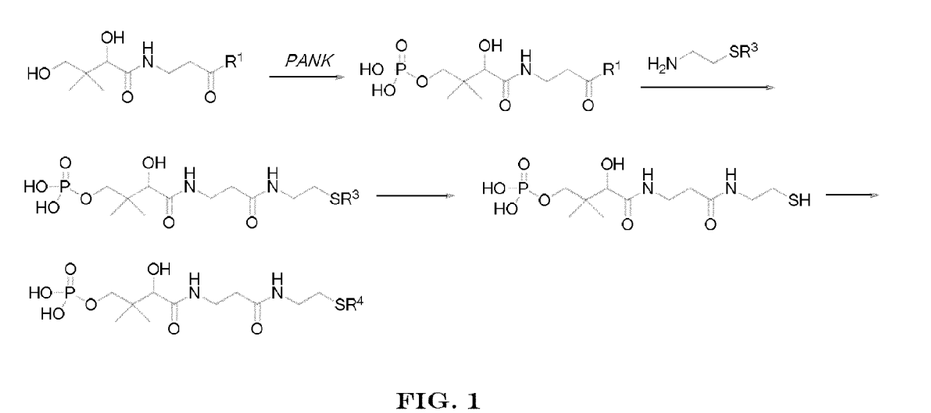
FIG. 1 shows a chemoenzymatic route to (S)-acyl-4'-phosphopantetheine derivatives according to the invention. PANK=pantothenate kinase; $R^1$, $R^3$, $R^4$ are not necessarily the same as $R_1$, $R_3$, $R_4$ as defined in the claims.
Figure 2:
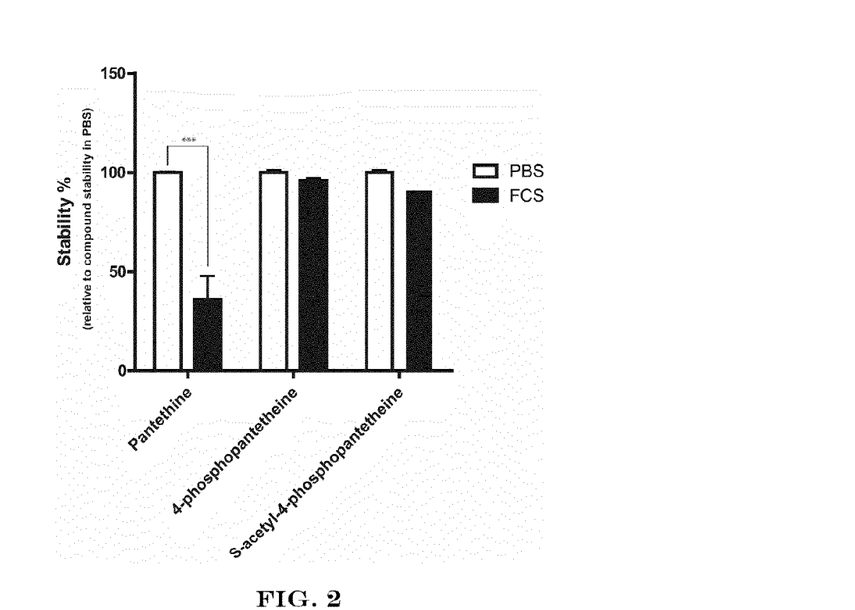
FIG. 2 shows improved stability of 4'-phosphopantetheine and (S)-acetyl-4'-phosphopantetheine in serum as compared to pantethine (Example 2). PBS, phosphate buffered saline; FCS, fetal calf serum.

Results: Pantethine is significantly degraded (60%), most likely by pantetheinase, whereas (S)-acetyl-4'-phosphopantetheine and 4'-phosphopantetheine are stable and degrade by less than 10%. The Experiment was performed in triplicate, error bars indicate standard deviation in FIG. 2.

Example 3: Rescue Potential of 4'-phosphopantetheine and (S)-acetyl-4'-phosphopantetheine in Cellular PKAN Disease Model The down-regulation of dPANK/fbl (PANK ortholog in Drosophila) using RNAi approach in Drosophila S2 cells is an established in-vitro PKAN disease model (Rana, A. et al., PNAS, 2010, 107, 6988; Siudja et al., EMBO Mol med. 2011, 3, 755; Siudeja et al., PLoS One 2012, 7, e443145). Down-regulation of dPANK/fbl by RNAi, causes a decrease in the survival of cells. A rescuing compound such as pantethine, 4'-phosphopantetheine or (S)-acetyl-4'-phosphopantetheine restores the cell survival. The following example is included to compare the rescue efficiency of pantethine, (S)-acetyl-4'-phosphopantetheine and 4'-phosphopantetheine in such model system.

Materials and Methods: Drosophila Schneider's S2 cells were cultured and subjected to RNAi treatment as described previously (Rana, A. et al., 2010, 107, 6988.). 100 μM of pantethine, (S)-acetyl-4'-phosphopantetheine and 4'-phosphopantetheine was added to the cells and the rescue potential was assessed by determining the cell survival.

Figure 3:
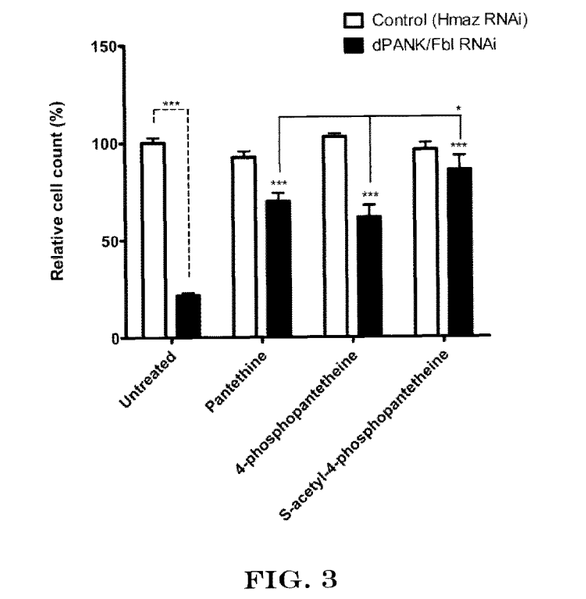
FIG. 3 shows that the rescue potential of 4'-phosphopantetheine and (S)-acetyl-4'-phosphopantetheine as compared to pantethine in a PKAN cell model (Example 3). (S)-acetyl-4'-phosphopantetheine is most effective.

Result: The result is shown in FIG. 3. The Figure indicates that both (S)-acetyl-4'-phosphopantetheine and 4'-phosphopantetheine rescued the cell count defect significantly in dPANK/fbl down-regulated Drosophila-S2 cells. (S)-acetyl-4'-phosphopantetheine is surprisingly found to have superior rescue potential as compared to pantethine and 4'-phosphopantetheine. Experiment was performed in triplicate, error bars indicate standard deviation.

Example 4: Rescue Potential in HOPAN Assay

In an additional experiment, Drosophila-S2 cells treated with the chemical inhibitor HOPAN (hopanthenate, CAS 17097-76-6, IUPAC: calcium 4-[[(2R)-2,4-dihydroxy-3,3-dimethylbutanoyl]amino]butanoate). Cells treated with HOPAN also serve as a model for PKAN. Cells treated with HOPAN also show a reduction in cell viability. Herewith, the result is included to compare the rescue efficiency of pantethine, (S)-acetyl-4'-phosphopantetheine and 4'-phosphopantetheine in such model system.

Materials and Methods: *Drosophila* Schneider's S2 cells were cultured and subjected to HOPAN (0.5 mM) treatment with and without (S)-acetyl-4'-phosphopantetheine and 4'-phosphopantetheine for two days (Siudeja. K. et al., EMBO Mol Med. 2011, 3, 755). 100 µM of (S)-acetyl-4'-phosphopantetheine and 4'-phosphopantetheine was compared for its rescue efficiency.

Figure 4:
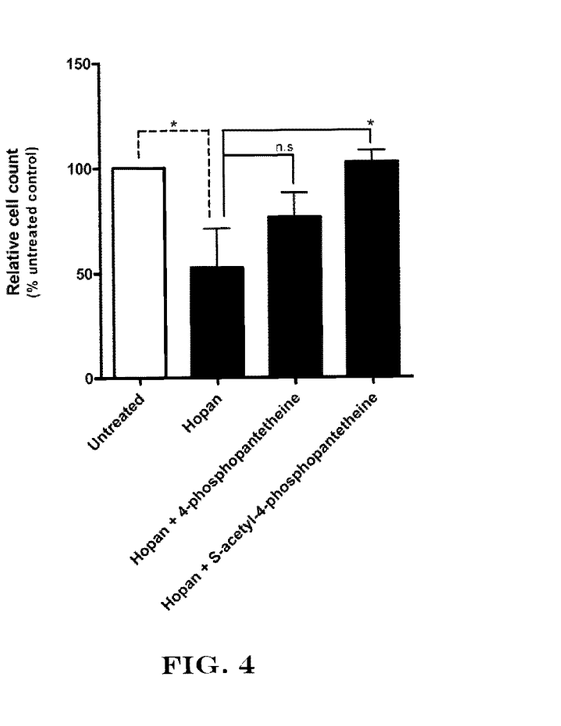
FIG. 4 shows the rescue potential of pantethine, 4'-phosphopantetheine and (S)-acetyl-4'-phosphopantetheine in cells treated with HOPAN (Example 4). (S)-acetyl-4'-phosphopantetheine is most effective.

Result: The result as shown below indicates (S)-acetyl-4'-phosphopantetheine significantly rescued the HOPAN (0.5 mM) induced cell count defect compared to 4'-phosphopantetheine. Experiment was performed in triplicate; error bars indicate standard deviation in FIG. 4.

Example 5: Rescue of HEK Cells in HOPAN Model

Similar to *Drosophila*-S2 cells, the PKAN disease model can also be induced using HOPAN in mammalian cell lines. Rescue efficiency of (S)-acetyl-4'-phosphopantetheine and 4'-phosphopantetheine was studied in HOPAN induced PKAN model system, namely in mammalian HEK293 cells.

Materials and Methods: HEK293 cells were cultured in vitamin B5 deficient DMEM (Thermo Scientific) supplemented with 10% dialysed FCS (Thermo Scientific) with and without HOPAN (0.5 mM) and (S)-acetyl-4'-phosphopantetheine and 4'-phosphopantetheine for 4 days. 100 µM of (S)-acetyl-4'-phosphopantetheine and 4'-phosphopantetheine was compared for its rescue efficiency.

Figure 5:
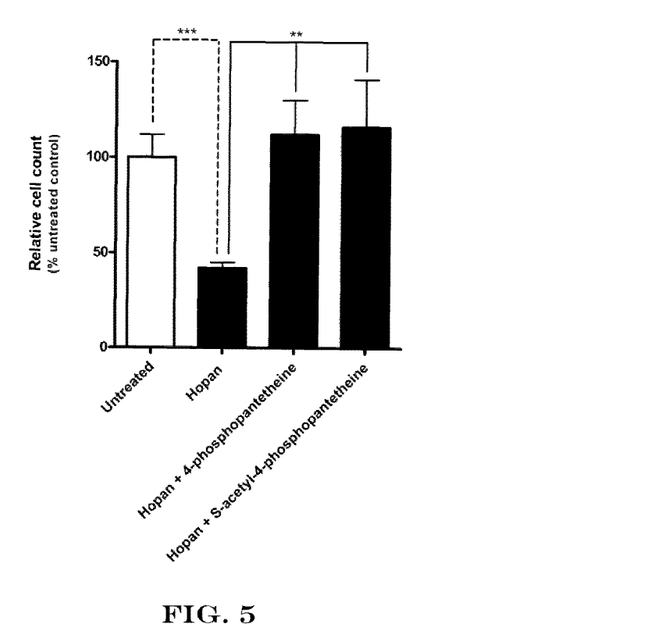
FIG. 5 shows the rescue of 4'-phosphopantetheine and (S)-acetyl-4'-phosphopantetheine in Human PKAN cell model treated with HOPAN (Example 5). 4'-phosphopantetheine and (S)-acetyl-4'-phosphopantetheine are potent rescue molecules.

Result: The result as shown below indicates (S)-acetyl-4'-phosphopantetheine and 4'-phosphopantetheine significantly reduced the HOPAN induced cell count defect also in mammalian-HEK293 cell system. Experiment was performed in triplicate; error bars indicate standard deviation in FIG. 5.

Example 6: Toxicity

Figure 6:
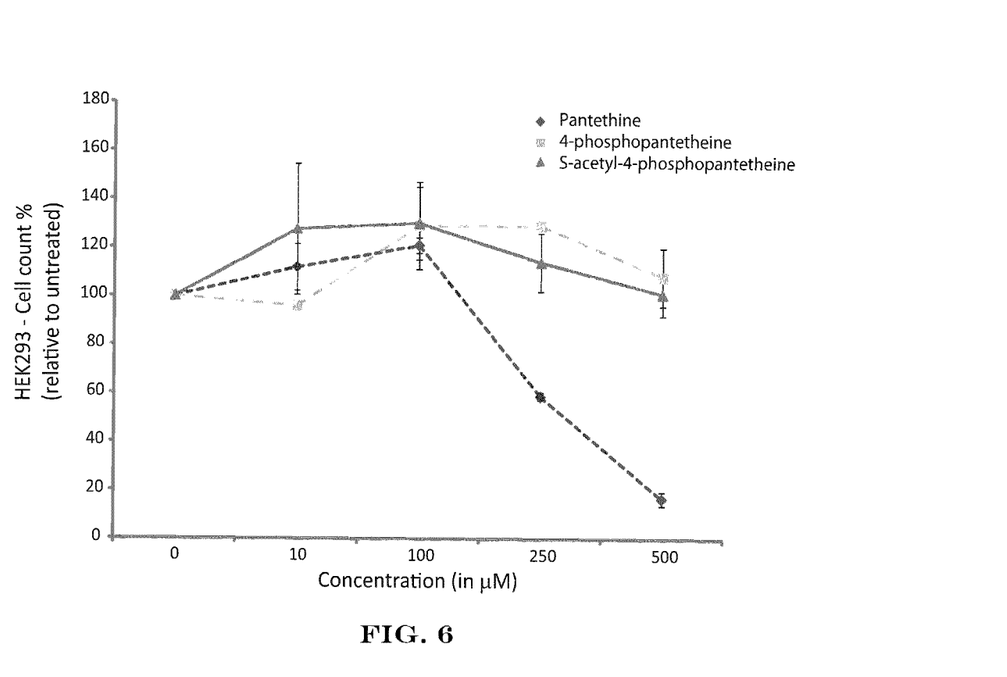
FIG. 6 shows a comparison of cellular toxicity of pantethine, 4'-phosphopantetheine and (S)-acetyl-4'-phosphopantetheine for human HEK293 cells (Example 6). Pantethine is more toxic compared to 4'-phosphopantetheine and (S)-acetyl-4'-phosphopantetheine.

Human HEK293 cells were treated with increasing concentrations of pantethine, 4'-phosphopantetheine and (S)-acetyl-4'-phosphopantetheine to determine and compare the toxicity of the compounds. A drop in cell counts indicates toxicity. Pantethine is inducing toxicity at lower concentrations compared to 4'-phosphopantetheine and (S)-acetyl-4'-phosphopantetheine, demonstrating that 4'-phosphopantetheine and (S)-acetyl-4'-phosphopantetheine are less toxic compared to pantethine. See FIG. 6.

Example 7: Preparation of bis(pivaloyloxymethyl)ester of S-acyl-4'-phosphopantetheine A phosphate-ester derivative according to the invention may be synthesized using the following procedure:

Iodomethyl pivalate is freshly prepared by reaction of chloromethyl pivalate (0.151 g, 1 mmol) with sodium iodide (0.3 g, 2 mmol) in acetonitrile (1 mL) at 30° C. for 5 h under $N_2$ atmosphere. To the reaction mixture is added dichloromethane (5 mL) and water (5 mL) and stirred. After phase separation the organic layer is washed with 2% aq. sodium thiosulfate ($Na_2S_2O_3$) and concentrated under vacuum to give iodomethyl pivalate as a yellowish oil 0.194 g (0.8 mmol, 80%). S-acetyl-4'-phosphopantetheine (0.04 g, 0.1 mmol) is suspended in DMF (1 mL). Triethylamine (0.042 mL, 0.3 mmol) and iodomethylpivalate (0.073 g, 0.3 mmol) are added. The mixture is stirred at around 40° C. overnight, then the solvent is removed and the residue dissolved in ethyl acetate. The mixture is washed with brine, dried over sodium sulfate, filtrated and concentrated under reduced pressure. Purification of the crude product is followed by column chromatography to give 0.016 g of bis(pivaloyloxymethyl) ester of S-acetyl-4'-phosphopantetheine (0.025 mmol, 25%).

Phosphate-ester derivatives of the invention have improved bio-availability, due to their increased membrane permeation potential.

Example 8: Alternative Method for Preparation of bis(pivaloyloxymethyl)ester of S-acyl-4'-phosphopantetheine Preparation of Phosphorylating Reagent

Bis(POM) chloro phosphate for the phosphorylation of S-acetil-pantetheine was prepared according to the published literature (Hwang Y et al., Organic Letters. 2004, 6, 1555; Ruda, G F et al., Chem Med Chem. 2007, 2, 1169):

Preparation of Tris(POM)phosphate

To a solution of trimethyl phosphate (7.01 g, 50 mmol) in dry $CH_3CN$ (42 mL) were sequentially added chloromethylpivalate (29.35 g, 195 mmol) and NaI (22.52 g, 150 mmol). The reaction mixture was heated at reflux (80° C.) for 72 hours, cooled to ambient temperature and diluted with $Et_2O$ (400 mL). The organic phase was washed with water (2×100 ml), saturated $Na_2S_2O_3$ solution (2×100 mL), dried over $Na_2SO_4$ and concentrated. Purification on silica gel eluting with hexane/EtOAc 4:1 afforded viscous yellow oil (14.6 g, 66%): $^1H$ NMR (300 MHz, $CDCl_3$) δ 5.66 (d, J=13.7 Hz, 6H), 1.24 (s, 27H) ppm; $^{31}P$ NMR (120 MHz, $CDCl_3$) δ −4.74 (s) ppm; HRMS (M+H$^+$) calculated for $C_{18}H_{34}O_{10}P$, 441.1890, found 441.1901.

Preparation of Bis(POM)hydrogen phosphate

Tris(POM) phosphate (1 g, 2.3 mmol) was dissolved in piperidine (7 mL) and stirred at room temperature for 12 h. The solution was concentrated and further evaporated in vacuo until constant weight. (935 mg, 99.0% yield). The crude oil (935 mg, 2.28 mmol) was dissolved in water (20 ml) and treated with Dowex W50X2 H$^+$ form resin (19.2 g, 11.4 mmol, 0.6 mmol/g). The suspension was stirred at ambient temperature for 1 hour. The resin was filtered and washed with water. The filtrate was concentrated and dried in vacuo affording a white solid (613 mg, 82% yield): $^1$H NMR (300 MHz, CDCl$_3$) δ 8.45 (bs, 1H), 5.62 (d, J=13.2 Hz, 4H), 1.23 (s, 18H) ppm; $^{31}$P NMR (120 MHz, CDCl$_3$) δ −3.17 (s) ppm.

Preparation of Bis(POM)chloro Phosphate

A solution of bis(POM) hydrogen phosphate (613 mg, 1.88 mmol) and DMF (7.3 μL, 0.094 mmol) in DCM (7.5 mL) was added dropwise to a stirred solution of oxalyl chloride (889 μL, 9.38 mmol) in DCM (7.5 mL) under argon at ambient temperature. Reaction mixture was stirred for 2 hours. The solvent was evaporated under argon to provide a crude yellow oil (671 mg, 1.86 mmol) which was directly used in the next step.

Preparation of S-acetyl phosphopantetheine bis[(pivaloyloxy)methyl]Ester

S-acetyl-pantetheine was prepared as described in [E. Walton et al., J. Am. Chem. Soc. 1954, 76, 1146]. To a stirred solution of S-acetil-pantetheine (463 mg, 1.45 mmol), N,N-iisopropylethylamine (308 μL, 1.77 mmol) and 4-Dimethylaminopyridine (10.9 mg, 0.09 mmol) in 10 ml of DCM at 0° C., was added dropwise under argon a solution of bis(POM) chloro phosphate (590 mg, 1.88 mmol) in 10 ml of DCM. Reaction mixture was allowed to warm to room temperature and stirred for 12 hours. The reaction was quenched with water (10 ml) and extracted with DCM (2×20 ml). Organic phase was washed with saturated solution of NH$_4$Cl, dried over Na$_2$SO$_4$ and concentrated under reduced pressure. Purification on silica gel eluting with DCM/MeOH, 92:8 afforded the product as a yellow oil (401 mg, 44% yield): $^1$H NMR (300 MHz, CDCl$_3$) δ 7.25 (app t, J=6.2 Hz, 1H), 6.39 (app t, J=5.3 Hz, 1H), 5.61-5.71 (m, 4H), 4.13 (dd, J=10.0, 6.9 Hz, 1H), 4.08 (d, J=6.3 Hz, 1H), 3.97 (d, J=5.8 Hz, 1H), 3.75 (dd, J=10.0, 7.2 Hz, 1H), 3.51-3.63 (m, 2H), 3.34-3.50 (m, 2H), 2.95-3.09 (m, 2H), 2.39-2.47 (m, 2H), 2.35 (s, 3H), 1.242 (s, 9H), 1.240 (s, 9H), 1.12 (s, 3H), 0.88 (s, 3H) ppm; $^{31}$P NMR (120 MHz, CDCl$_3$) δ −2.64 (s) ppm.

Example 9: Alternative Method for the Synthesis of 4'-phosphopantetheine

D-Pantothenic acid was prepared from its hemicalcium salt (Aldrich, ≥99.0%) reacting with oxalic acid. S-Trityl-cysteamine was synthesized from cysteamine hydrochloride and trityl chloride as reported by Mandel et al. [A. L. Mandel, et al., Org. Lett. 2004, 6, 26, 4801-4803]. Dibenzylchlorophosphate was prepared by reacting dibenzylphosphite with N-chlorosuccinimide as described by Itoh et al. [K. Itoh et al., Org. Lett. 2007, 9, 5, 879-882] in toluene as a solvent. All other chemicals were obtained from commercial sources and used without further purification; cysteamine hydrochloride (Aldrich, ≥98.0%), trityl chloride (Aldrich, 97.0%), N-(3-dimethylaminopropyl)-N'-ethylcarbodiimide (Aldrich, ≥97.0%), 1-hydroxybenzotriazole hydrate (Aldrich, ≥97.0%), dibenzylphosphite (Aldrich, technical grade), N-chlorosuccinimide (Aldrich, 98%). Column chromatography was carried out using Silica gel 60 Å, 60-100 mesh (Aldrich). Cation exchange chromatography was performed on DOWEX 50WX2, hydrogen form, 100-200 mesh (Aldrich). $^1$H and $^{13}$C NMR were recorded at 25° C. with Varian Unity Inova 300 MHz spectrometer (300 MHz/75 MHz). The chemical shifts (δ) are reported in ppm units relative to TMS as an internal standard where spectra recorded in CDCl$_3$ or relative to residual solvent signal when D$_2$O was used. High-resolution mass spectra were obtained on AutospecQ mass spectrometer with negative electrospray ionization.

a) Coupling Reaction—Synthesis of S-tritylpantetheine

In dried acetonitrile (100 mL) were prepared separately: (A) D-pantothenic acid (2.19 g, 10.0 mmol), (B) S-tritylcysteamine (3.19 g, 10.0 mmol) and (C) N-(3-dimethylaminopropyl)-N'-ethylcarbodiimide (1.55 g, 10.0 mmol) together with 1-hydroxybenzotriazole hydrate (1.35 g, 10.0 mmol). When mixed together (A), (B) and (C), triethylamine (10.4 mL, 75 mmol) was added. The mixture was stirred at room temperature for 24 h and quenched with addition of water. The product was extracted with diethyl ether. The combined organic phases were washed with 1 M hydrochloric acid, saturated aqueous solution of NaHCO$_3$ and brine. Organic layer was dried over sodium sulfate and concentrated in vacuum to give S-tritylpantetheine (3.53 g, 68%) as pale-yellow crystals. $^1$H NMR (300 MHz, CDCl$_3$) δ 0.85 (s, 3H), 0.92 (s, 3H), 2.29 (t, J=6.2 Hz, 2H), 2.38 (t, J=6.4 Hz, 2H), 3.03 (dd, J=6.0, 5.2 Hz, 2H), 3.45 (m, 4H), 3.92 (s, 1H), 6.20 (t, J=5.7 Hz, 1H, NH), 7.21 (m, 3H), 7.27 (m, 6H), 7.39 (m, 6H).

b) Phosphorylation—Synthesis of
S-trityl-4'-dibenzylphosphopantetheine

Dibenzylchlorophosphate was freshly prepared by reaction of dibenzylphosphite (2.16 g, 8.24 mmol) with N-chlorosuccinimide (1.21 g, 9.06 mmol) in toluene (40 mL) at room temperature for 2 h. The mixture was filtered and the filtrate was evaporated under vacuum and added to a solution of S-tritylpantetheine (2.86 g, 5.49 mmol), diisopropylethylamine (3.06 mL), 4-dimethylaminopyridine (0.067 g, 0.55 mmol) in dry acetonitrile. The mixture was stirred for 2 h at room temperature. Products were extracted into organic phase in dichloromethane—aqueous $NaHCO_3$ system. The organic extracts were washed with water and brine, and dried over $Na_2SO_4$. Evaporation of solvent gave a crude S-trityl-4'-dibenzylphosphopantetheine as a dark brown oil (4.69 g), which was further purified by flash chromatography to give a semicrystalline pale yellow product (0.640 g, 0.82 mmol). The yield of the synthesis and purification of S-trityl-4'-dibenzylphosphopantetheine is 15%. $^1$H NMR (300 MHz, $CDCl_3$) δ 0.75 (s, 3H), 1.03 (s, 3H), 2.32 (t, J=6.1 Hz, 2H), 2.4 (t, J=6.5 Hz, 2H), 3.06 (dd, J=6.5, 6.2 Hz, 2H), 3.47 (dd, J=6.1, 6.0 Hz, 2H), 3.60 (dd, J=9.9, 7.3 Hz 1H), 3.85 (s, 1H), 4.00 (dd, J=9.9, 7.0 Hz, 1H), 5.04 (m, 4H), 5.80 (t, J=5.5 Hz, 1H, NH), 7.18-7.42 (m, 25H).

c) Deprotection—Synthesis of
4'-phosphopantetheine

Naphthalene (12.9 g, 100.6 mmol) dissolved in tetrahydrofuran (70 mL) was added to sodium metal (2.21 g, 96.1 mmol) in tetrahydrofuran (50 mL). After 2 h the solution was cooled to −(35±5)° C. and S-trityl-4'-dibenzylphosphopantetheine (1.85 g, 2.37 mmol) dissolved in tetrahydrofuran (70 mL) was slowly added. The mixture was stirred for a 2 h while maintaining the temperature below −30° C. The reaction was quenched by addition of water and then dichloromethane was added. Aqueous phase was washed with dichloromethane and diethylether, concentrated under vacuum and passed through cation exchange column (DOWEX 50WX2). Fractions were analyzed by LCMS and those containing the product were pooled and concentrated under vacuum. 4'-phosphopantetheine was precipitated with addition of $Ca(OH)_2$ as a calcium salt (332 mg, 0.838 mmol, 35%). The structure of the product was confirmed by comparison of NMR data with the literature [Lee, C-H. et al., J. Am. Chem. Soc. 1975, 1225-1236] and by HRMS. $^1$H NMR (300 MHz, $D_2O$) δ 0.86 (s, 3H), 1.08 (s, 3H), 2.54 (t, J=6.3 Hz, 2H), 2.87 (t, J=6.3 Hz, 2H), 3.43 (dd, J=10.3, 5.0 Hz, 1H), 3.54 (m, 4H), 3.76 (dd, J=10.3, 6.5 Hz, 1H), 4.14 (s, 1H). The HRMS mass for $C_{11}H_{22}N_2O_7SP$ [M−H]$^−$ was found to be 357.0880, which corresponds to the expected mass of 357.0885.

The invention claimed is:

1. A method of treating pantothenate kinase-associated neurodegeneration (PKAN), comprising administering to a subject in need thereof a therapeutically effective amount of a compound having the structural formula:

(Structure I)

wherein:

$R_1$ is —H, unsubstituted or substituted alkyl, unsubstituted or substituted alkenyl, substituted or unsubstituted cycloalkyl, substituted or unsubstituted aryl, substituted or unsubstituted arylalkyl, substituted or unsubstituted non-aromatic heterocyclyl, substituted or unsubstituted aromatic heterocyclyl, substituted or unsubstituted heterocyclylalkyl, —$COR_{11}$, —C(O)$OR_{11}$, —C(O)$NR_{11}R_{12}$, —C=$NR_{11}$, —CN, —$OR_{11}$, —OC(O)$R_{11}$, —$NR_{11}R_{12}$, —$NR_{11}$C(O)$R_{12}$, —$NO_2$, —N=$CR_{11}R_{12}$ or -halogen;

$R_2$ and $R_3$ are independently selected from the group consisting of: —H, -methyl, -ethyl, -phenyl, acetoxymethyl (AM), pivaloyloxymethyl (POM), $R_2$ and $R_3$ jointly form a structure selected from the group consisting of:

[structures]

wherein
$R_4$ is —H or -alkyl;
$R_5$ is —H or -alkyl;
$R_6$ is —H, -alkyl, or —CH$_2$(CO)OCH$_3$;
$R_7$ is —H, -alkyl or -halogen;
$R_8$ is —H or -alkyl;
$R_9$ is —H, -alkyl;
$R_{10}$ is —H, -alkyl;
$R_{11}$ and $R_{12}$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, or halogen;
or a pharmaceutically acceptable salt or solvate thereof.

2. The method of claim 1, wherein in the compound of structure I, $R_2$ and $R_3$ are each H.

3. The method of claim 1, wherein in the compound of structure I, $R_1$ is methyl.

4. The method of claim 1, wherein in the compound of structure I, $R_1$ is methyl, and $R_2$ and $R_3$ are each H.

5. The method of claim 1, wherein the compound of structure I is a D stereoisomer.

6. The method of claim 1, wherein the compound of structure I is a D stereoisomer, in which $R_1$ is methyl, and $R_2$ and $R_3$ are each H.

7. The method of claim 1, wherein the pharmaceutically acceptable salt or solvate of the compound of structure I is a calcium salt.

8. The method of claim 1, wherein the compound of structure I is a D stereoisomer, in which $R_1$ is methyl, and $R_2$ and $R_3$ are each H, and wherein the pharmaceutically acceptable salt or solvate thereof is a calcium salt.

\* \* \* \* \*